United States Patent
Gauthier et al.

(10) Patent No.: US 9,943,988 B1
(45) Date of Patent: Apr. 17, 2018

(54) REUSABLE SURGICAL IMPLEMENT

(71) Applicant: Gauthier Biomedical, Inc., Grafton, WI (US)

(72) Inventors: Michael T. Gauthier, Grafton, WI (US); Kenneth Roggow, Milwaukee, WI (US); Mara C. Schwartz, Glendale, WI (US); Austin R. Braganza, Milwaukee, WI (US)

(73) Assignee: Gauthier Biomedical, Inc., Grafton, WI (US)

( * ) Notice: Subject to any disclaimer, the term of this patent is extended or adjusted under 35 U.S.C. 154(b) by 490 days.

(21) Appl. No.: 14/317,337

(22) Filed: Jun. 27, 2014

Related U.S. Application Data (63) Continuation-in-part of application No. 14/273,782, filed on May 9, 2014, which is a continuation-in-part of application No. 14/168,600, filed on Jan. 30, 2014, which is a continuation of application No. 12/538,439, filed on Aug. 10, 2009, now Pat. No. 8,641,955.

(60) Provisional application No. 61/087,365, filed on Aug. 8, 2008, provisional application No. 61/993,383, filed on May 15, 2014, provisional application No. 61/840,299, filed on Jun. 27, 2013.

(51) Int. Cl.
  *A61F 2/46*     (2006.01)
  *B29C 31/00*    (2006.01)
  *A61B 17/88*    (2006.01)

(52) U.S. Cl.
  CPC ............ *B29C 31/008* (2013.01); *A61B 17/88* (2013.01); *A61F 2/4684* (2013.01); *A61F 2240/007* (2013.01)

(58) Field of Classification Search
  None
  See application file for complete search history.

(56) References Cited

U.S. PATENT DOCUMENTS

| | | | |
|---|---|---|---|
| 2,298,365 A | 10/1942 | Gits et al. | |
| 4,495,130 A | 1/1985 | Hedrick | |
| 4,889,107 A * | 12/1989 | Kaufman ............... | A61B 17/02 128/850 |
| 5,390,572 A | 2/1995 | Gakhar et al. | |
| 5,882,567 A | 3/1999 | Cavallaro et al. | |
| 6,183,681 B1 | 2/2001 | Sullivan et al. | |
| 6,228,306 B1 | 5/2001 | Hoepfl et al. | |
| 2003/0135223 A1 * | 7/2003 | Teague .................. | A61B 17/221 606/127 |
| 2005/0065542 A1 * | 3/2005 | Mansfield .......... | A61B 17/3205 606/167 |

(Continued)

FOREIGN PATENT DOCUMENTS

EP  2018830  *  1/2009

*Primary Examiner* — Edmund Lee
(74) *Attorney, Agent, or Firm* — Boyle Fredrickson, S.C.

(57) ABSTRACT

A reusable surgical implement is provided that is formed of a core positioned within an enclosure. The core is formed of a suitable flexible material to enable the implement, which can be any suitable device such as a reusable surgical trial implant, rod template or flex driver, among others, to be bent to conform to the desired shape for an actual implant to be placed in the location of the implement. The material forming the enclosure is also flexible to accommodate the flexing of the core, and is biologically inert to enable the implement to be sterilized after use for use in subsequent surgical procedures.

7 Claims, 6 Drawing Sheets

(56) References Cited

U.S. PATENT DOCUMENTS

| | | |
|---|---|---|
| 2006/0026800 A1 | 2/2006 | Lawless |
| 2007/0290399 A1* | 12/2007 | Easter .................... B25B 15/02 264/255 |
| 2008/0114303 A1* | 5/2008 | Tremaglio ............ A61M 25/09 604/164.13 |

* cited by examiner

REUSABLE SURGICAL IMPLEMENT

CROSS-REFERENCE TO RELATED APPLICATIONS

This application claims priority as a continuation-in-part U.S. Non-Provisional patent application Ser. No. 14/273,782, filed on May 9, 2014, which is a continuation-in-part of U.S. Non-Provisional patent application Ser. No. 14/168,600, filed on Jan. 30, 2014, which in turn is a continuation of U.S. Non-Provisional patent application Ser. No. 12/538,439, filed on Aug. 10, 2009, now U.S. Pat. No. 8,641,955, issued on Feb. 4, 2014, which claims priority from U.S. Provisional Application Ser. No. 61/087,365 filed on Aug. 8, 2008, as well as from U.S. Provisional Patent Application Ser. No. 61/993,383, filed May 15, 2014, and from U.S. Provisional Application Ser. No. 61/840,299, filed on Jun. 27, 2013, the entirety of which are each hereby expressly incorporated by reference herein.

FIELD OF THE INVENTION

The present invention relates generally to implements utilized in surgical procedures and more specifically to reusable implements utilized in surgical procedures.

BACKGROUND OF THE INVENTION

There are many types of implements that are used in surgical procedures. The implements, such as implants, provide a physician with the ability to stabilize portions of the body that are being repaired in a surgical or medical procedure.

Oftentimes, the physician needs to determine the proper location and orientation for the implant prior to actually positioning and securing the implant within the body. To do so, a trial or template implant is utilized. This trial or template implant is formed of titanium with an anodized exterior coating (e.g., Ti06AL-4V), and is formed with a configuration similar to the form of the actual implant to be secured within the body. In use, the trial or template implant is placed within the body and manipulated by the physician to determine the proper location for the actual implant. Once determined, the location can be marked and the actual implant affixed within the body using known procedures.

However, with these prior art trial or template implants, the nature of the anodized titanium used to form them requires that the trial or template implant be used only once and then discarded. The reason for this is that the anodized coating, which is necessary for trial or template implants formed of titanium, can become brittle or otherwise damaged upon sterilization after an initial use. Thus, the coating can flake off during subsequent uses and consequently endanger the patient.

In addition, other implements that are designed for use in various surgical procedures are formed of rigid materials. These constructions make it difficult for medical practitioners to use devices of this type in confined spaces, and can result in the individual having to use the implement at an awkward angle. Also, in other implements of this type formed with flexible structures, the implements have exposed springs or coils which could trap debris, making the element hard to clean for subsequent uses. Further, some flexible implements have tubing sleeves which cover the flexible coils or springs, but these tubes do not closely conform to the shape of the coils and/or springs, providing a space between the flexible element and the tube within which debris can be trapped.

Thus, it is desirable to develop implements for surgical procedures, such as trial or template implants, that is formed of a material that is flexible in nature and that can be sterilized and reused in multiple procedures.

SUMMARY OF THE INVENTION

Briefly described, one aspect of the present disclosure provides a reusable surgical implement, such as a trial or template implant, a rod template or flex driver, among others, formed of a substantially rigid, but flexible core material that is enclosed within an inert material that is capable of being sterilized after use to enable the implement to be reused. In the case of a trial implant, the inert material is molded over the core material to conform to the shape of the actual implant to provide the appropriate representation of the actual implant to be placed within the body of the patient. Once used, the trial implant can be removed and placed with the actual implant, with the trial implant being subsequently sterilized, such as in an autoclave, for additional uses.

According to another aspect of the present disclosure, the inert material is flexible to accommodate the flexibility of the core material while maintaining the core enclosed within the inert material. Thus, the implement can be bent in order to accurately represent the proper location and configuration or use of the actual implement within the body. In addition, the material allows for implements having other uses, such as flex drivers, to be shaped and/or oriented as necessary with the inert material maintaining conformance with the flexible core material for a physician to accurately locate the implement and drive a fastener used in the procedure when presented with hard to reach areas or angles during the procedure. After use, the inert material enables the flex driver to be cleaned and/or sterilized for further uses without damaging the core material, components and mechanism(s)

Numerous other aspects, features, and advantages of the present invention will be made apparent from the following detailed description together with the drawing figures.

BRIEF DESCRIPTION OF THE DRAWINGS

The drawings illustrate the best mode currently contemplated of practicing the present invention.

In the drawings.

DETAILED DESCRIPTION OF THE INVENTION

Figure 1:
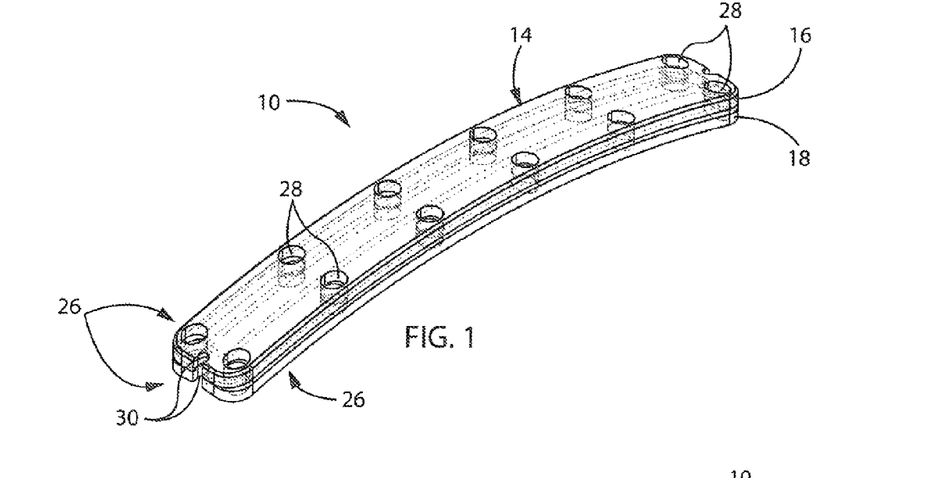
FIG. 1 is an isometric view of a one exemplary embodiment of a reusable surgical implement constructed according to the present disclosure.

Referring now in detail to the drawing figures, wherein like reference numerals represent like parts throughout the several views, one exemplary embodiment of a reusable surgical implement, formed as a trial or template implant constructed according to the present disclosure is illustrated generally at 10 in FIG. 1. As best shown in FIGS. 1-8, the implant 10 is formed of a central core 12 and an enclosure 14 disposed around the core 12 formed of an upper portion 16 and a lower portion 18. In the illustrated embodiment, the implant 10 is formed with a pre-curved shape, though other configurations for the implant 10 as also contemplated as being within the scope of the disclosure of the present invention.

Figure 2:
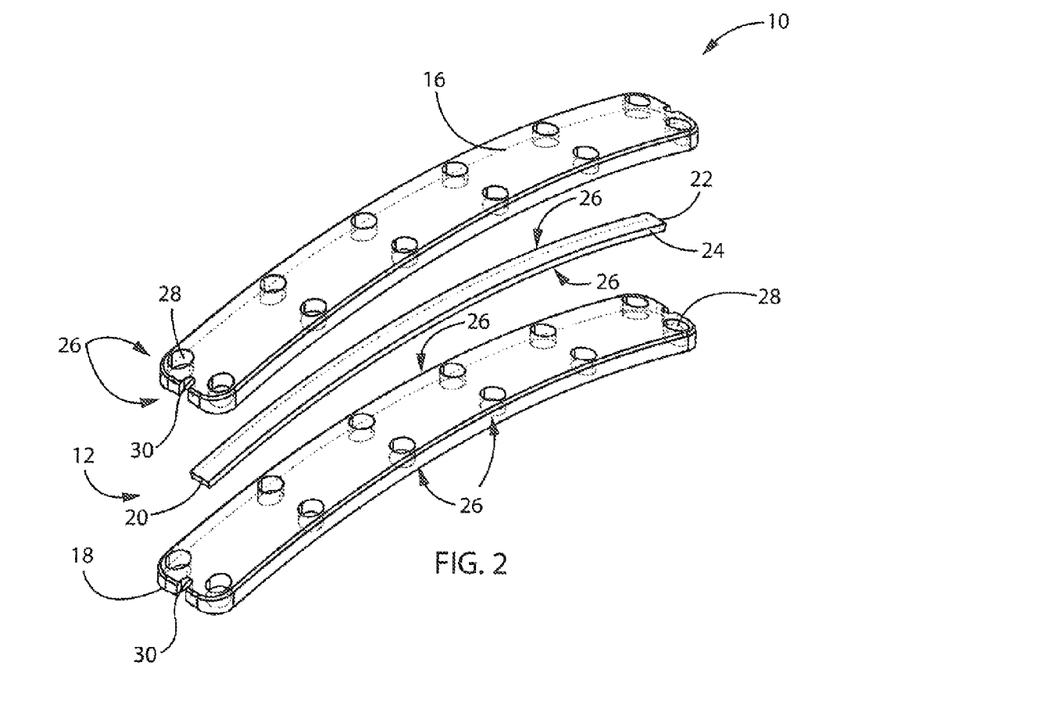
FIG. 2 is a an exploded view of the trial implant of FIG. 1.
Figure 3:
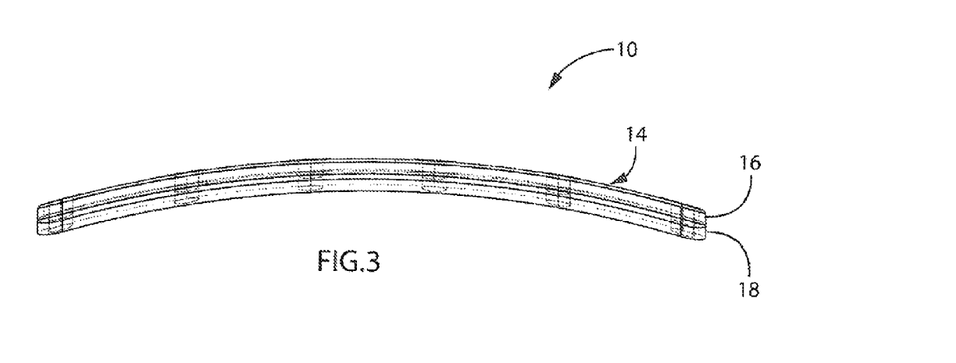
FIG. 3 is a side elevation view of the trial implant of FIG. 1.
Figure 4:
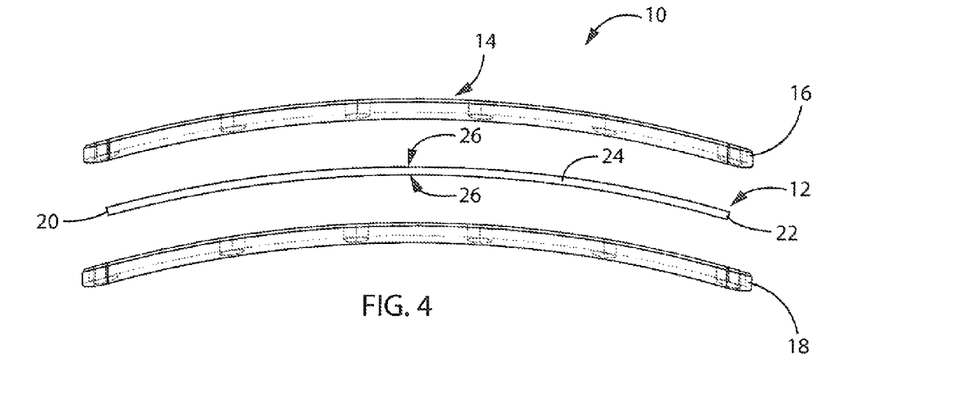
FIG. 4 is an exploded view of the trial implant of FIG. 3.
Figure 5:
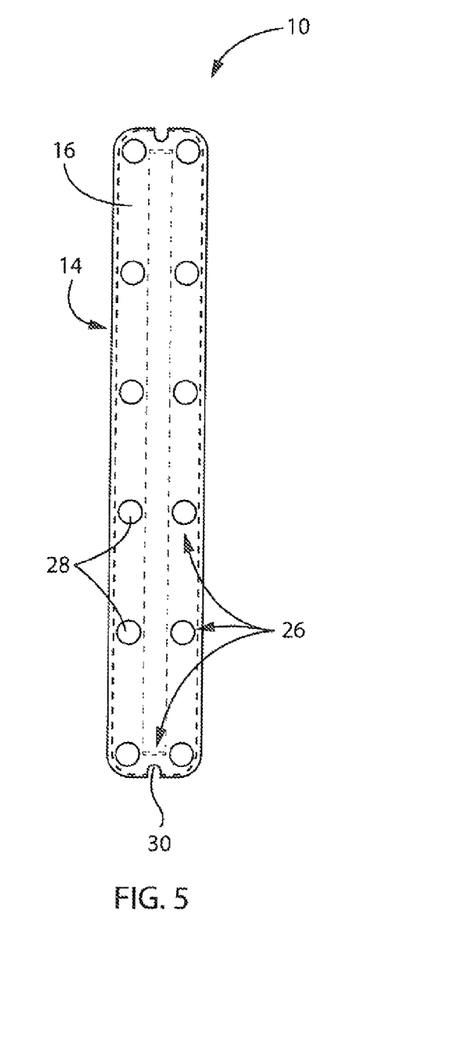
FIG. 5 is a top plan view of the trial implant of FIG. 1.
Figure 6:
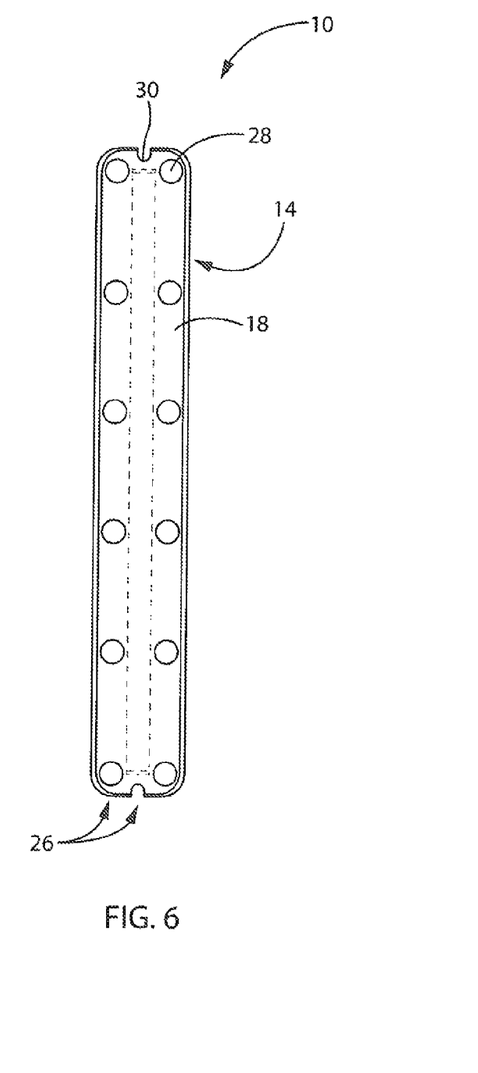
FIG. 6 is a bottom plan view of the trial implant of FIG. 1.
Figure 7:
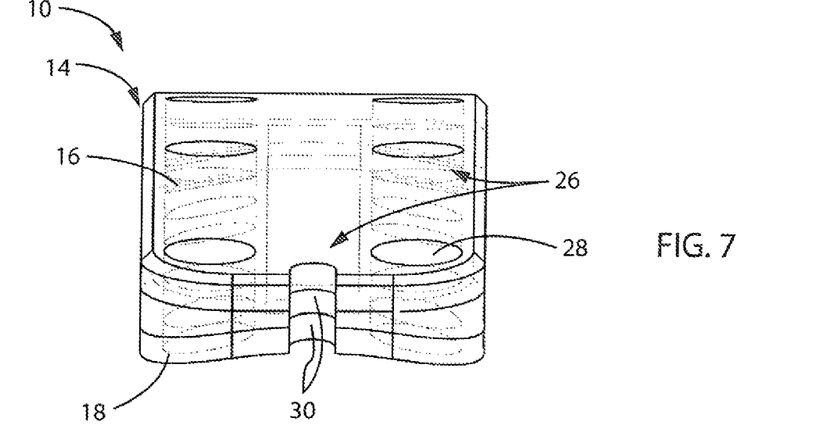
FIG. 7 is an end elevation view of the trial implant of FIG. 1.
Figure 8:
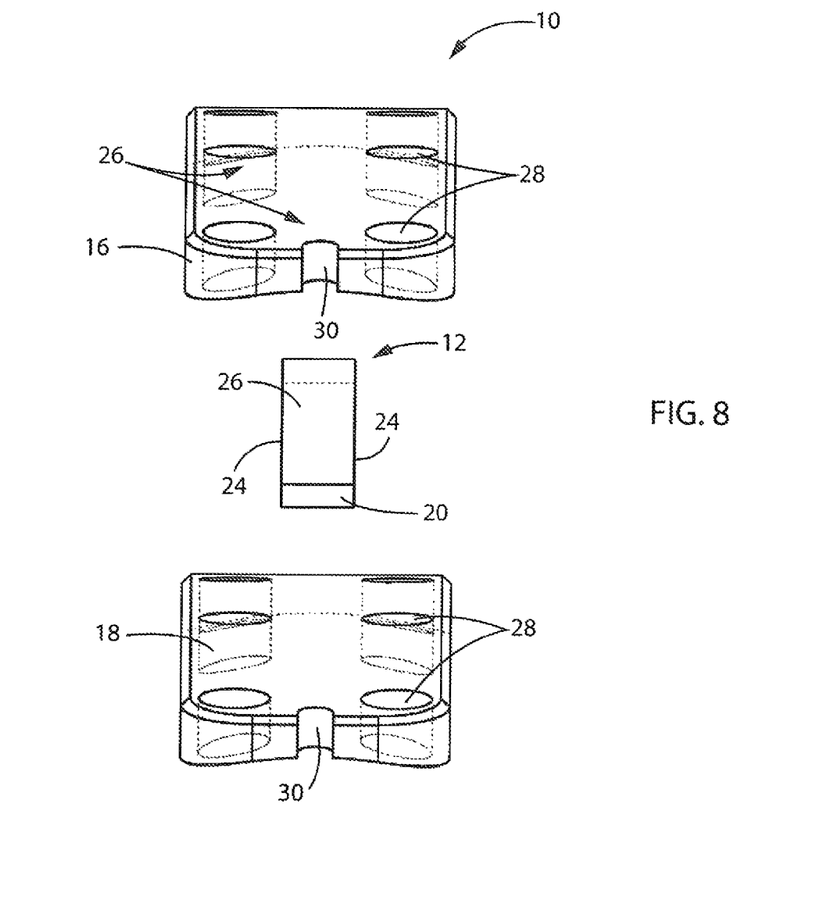
FIG. 8 is an exploded view of the trial implant of FIG. 7.

Referring now to FIGS. 2, 4 and 8, though any suitable shape for the core 12 can be utilized, in the illustrated embodiment the core 12 is formed with a generally rectangular configuration with a first end 20 and a second end 22 joined by opposed sides 24. In the illustrated embodiment the core 12 is also formed to be generally rectangular in cross-section with a pair of generally flat opposed surfaces 26 joining the ends 20, 22 and the sides 24, though any suitable cross-sectional shape can be utilized to impart the desired amount of flexibility to the core 12. The core 12 is shaped in any suitable machine and/or process to provide the desired shape for the core 12, which may include apertures or other features therein, as desired.

The material forming the core 12 is selected to be a generally rigid, but flexible material that can be altered in shape by applying a physical force to the core 12. Once, the force is removed, the core 12 remains in the shape to which it was altered by the applied force. In one embodiment of the core 12, the core 12 is formed of a shape memory material, such as a shape memory metal alloy, including the materials marketed under the trade name Nitinol® by Nitinol Devices & Components, Inc. of Fremont, Calif.

The enclosure 14 is disposed around the core 12 and each portion 16 and 18 of the enclosure 14 is formed of a biologically inert and flexible material that can conform to the shape of the core 12 in any configuration for the core 12. In one embodiment, the material forming the portions 16 and 18 of the enclosure 14 is a silicone, such as a silicone rubber, including a high consistence rubber (HCR).

The portions 16 and 18 of the enclosure 14 are formed with features 26 that are identical or at least similar to those of the actual implant (not shown) to be secured within the body of the patient, to provide an accurate representation of the proper location of the actual implant in the body. The features 26 can include apertures 28 and notches 30, among others. The apertures 28 can extend completely through the respective portions 16 and 18 without intersecting the core 12, thereby preserving the integrity of the enclosure 14 around the core 12. Further, the shape of the portions 16 and 18 forming the enclosure 14 can be shaped as desired to approximate the shape of the actual implant. Also, the shape of the portions 16 and 18 can be selected independently of the shape of the core 12, or to conform to the shape of the core 12, as desired.

In one embodiment, the trial implant 10 is formed by initially forming the core 12 of the desired material in any suitable manner, such as by extruding or molding the material into the desired shape for the core 12. The core 12 is then placed within a suitable mold to enable the material selected form either the upper portion 16 or the lower portion 18 to be introduced into the mold containing the core 12 and forma portion of the enclosure 14 on or over the core 12 that contains the desired features 26. Any suitable molding process can be utilized to form the upper portion 16 or lower portion 18 around the core 12.

Subsequently, the core 12 and the portion 16 or 18 molded onto or over the core 12 are removed or transferred from the first mold and placed within a separate or second mold used to form the other of the upper portion 16 or the lower portion 18 on or over the core 12 in connection with the first portion 16 or 18 and with the desired features 26. The material selected to form the other portion 16 or 18 can be selected to be the same or different than the material used to form the first portion 16 or 18, to provide the desired attributes to the enclosure 14 and the implant 10, so long as the materials forming the upper portion 16 and lower portion 18 are capable of mating, co-mingling or otherwise joining to one another in the molding process to form the enclosure 14 around the core 12. Additionally, suitable materials can be applied to one or both of the portions 16 and/or 18 to properly affix the portions 16 and 18 to one another, either during molding of the portions 16 and 18 to one another, or when affixing pre-molded portions 16 and 18 to one another around the core 12.

In alternative embodiments, the portions 16 and 18 can be formed subsequently or simultaneously within a single mold in any suitable molding process.

In use, the implant 10 in a sterile condition is placed within the body of a patient and bent, such as by hand, to conform the implant 10 to the shape desired for the actual implant within the body. In this position and shape, the location for suitable securing members, such as screws, are marked using the positions of the various features 26 formed in the implant 10. The implant 10 can then be removed and replaced by the actual implant which is affixed within the body of the patient using the marked locations for the securing members.

Once removed from the body, the implant 10 can be cleaned and sterilized for additional uses. When sterilized, the heat used to sterilize the implant 10 can also activate the material forming the core 12 to return the implant 10 to its initial pre-bent configuration or shape, thus making the implant 10 ready for use once the sterilization process has been completed.

As best shown in FIGS. 9-17, a second exemplary embodiment of the implement is formed as a rod template 100 having a central core 12' and an enclosure 14' disposed around the core 12' formed of a first component or portion(s) 16' and a second component or portion(s) 18'. In the illustrated embodiment, the rod template 100 is formed similarly to the implant 10, and can be generally straight, though other configurations for the rod template 100 are also contemplated as being within the scope of the disclosure of the present invention.

Though any suitable shape for the core 12' can be utilized, in the illustrated embodiment the core 12' is formed with a generally flat rectangular or cylindrical cross-sectional shape with a first end 20' and a second end 22' joined by opposed sides 24', though any suitable cross-sectional shape can be utilized to impart the desired amount of flexibility to the core 12'. The core 12' is shaped in any suitable machine and/or process to provide the desired shape for the core 12', which may include apertures or other features therein, as desired.

The material forming the core 12' is selected to be a generally rigid, but flexible material that can be altered in shape by applying a physical force to the core 12'. Once, the force is removed, the core 12' remains in the shape to which it was altered by the applied force. In one embodiment of the core 12', the core 12' is formed of a shape memory material, such as a shape memory metal alloy, including the materials marketed under the trade name Nitinol® by Nitinol Devices & Components, Inc. of Fremont, Calif.

The enclosure 14' is disposed around the core 12' and each portion 16' and 18' of the enclosure 14' is formed of a biologically inert and flexible material that can conform to the shape of the core 12' in any configuration for the core 12'. In one embodiment, the material forming the portions 16' and 18' of the enclosure 14' is a silicone, such as a silicone rubber, including a high consistence rubber (HCR).

The portions 16' and 18' of the enclosure 14' are formed with any features (not shown) desired to enhance the utility of the implement 100 when utilized within the body of the patient. The features can include apertures (not shown) and notches (not shown), among others. The apertures can extend completely through the respective portions 16' and 18' without intersecting the core 12', thereby preserving the integrity of the enclosure 14' around the core 12'. Further, the shape of the portions 16' and 18' forming the enclosure 14' can be shaped as desired. Also, the shape of the portions 16' and 18' can be selected independently of the shape of the core 12', or to conform to the shape of the core 12', as desired.

Figure 9:
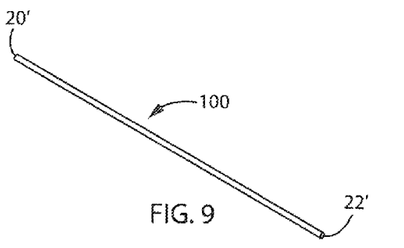
FIG. 9 is an isometric view of another exemplary embodiment of a reusable surgical implement constructed according to the present disclosure.
Figure 10:
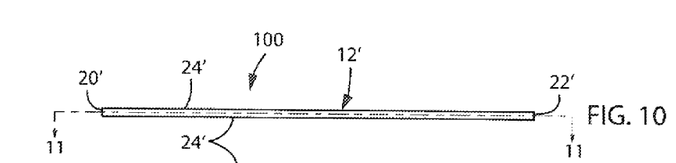
FIG. 10 is a side elevation view of the implement of FIG. 9.
Figure 11:
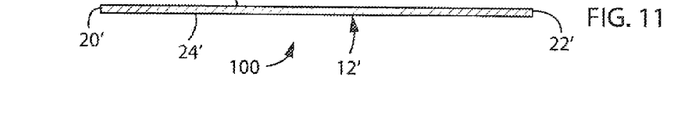
FIG. 11 is a cross-sectional view along line 11-11 of FIG. 10.
Figure 12:
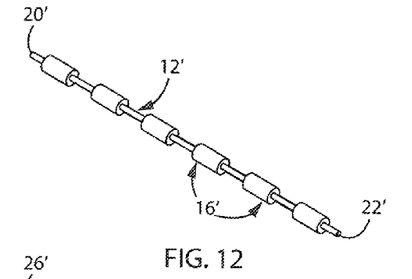
FIG. 12 is an isometric view of the implement of FIG. 9 after a first molding step.
Figure 13:
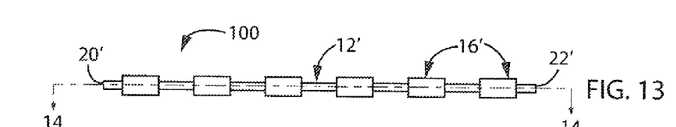
FIG. 13 is a side elevation view of the implement of FIG. 12.
Figure 14:
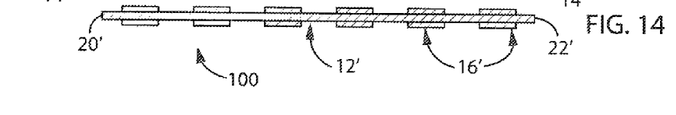
FIG. 14 is a cross-sectional view along line 14-14 of FIG. 13.

In the illustrated embodiment, the implement 100 is formed by initially forming the core 12' of the desired material in any suitable manner, such as by extruding or molding the material into the desired shape for the core 12', as shown in FIGS. 9-11. The core 12' is then placed within a suitable mold to enable the material selected to form the first portion 16' to be introduced into the mold containing the core 12' and form a portion of the enclosure 14' on or over the core 12' that contains the desired features. Any suitable molding process can be utilized to form the first portion 16' around the core 12', such as those shown in commonly owned U.S. Pat. No. 8,641,955 and its related applications, each of which are expressly incorporated by reference herein in their entirety. In the illustrated embodiment best shown in FIGS. 12-14, the first portion 16' constitutes a number of spaced sections 102 disposed along the length of the core 12'.

Subsequently, the core 12' and the first portion 16' molded onto or over the core 12' are removed or transferred from the first mold and placed within a separate or second mold used to form the other of the second portion 18' on or over the core 12' in connection with the first portion 16' and with the desired features. The material selected to form the second portion 18' can be selected to be the same or different in one or more respects or attributes than the material used to form the first portion 16', in order to provide the desired attributes to the enclosure 14' and the implement 100, so long as the materials forming the first portion 16' and second portion 18' are capable of mating, co-mingling or otherwise joining to one another in the molding process used to form the enclosure 14' around the core 12', which can be the same or different that the process used to form the first section 16'. Additionally, suitable materials can be applied to one or both of the portions 16' and/or 18' to properly affix the portions 16' and 18' to one another, either during molding of the portions 16' and 18' to one another, or when affixing pre-molded portions 16' and 18' to one another around the core 12'.

Figure 15:
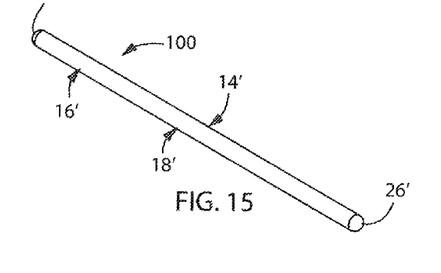
FIG. 15 is an isometric view of the implement of FIG. 9 after a second molding step.
Figure 16:
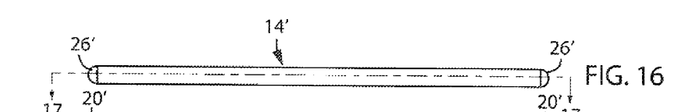
FIG. 16 is a side elevation view of the implement of FIG. 15.
Figure 17:
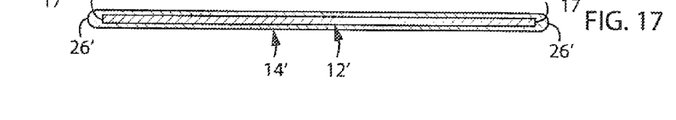
FIG. 17 is a cross-sectional view along line 17-17 of FIG. 16.
Figure 18:
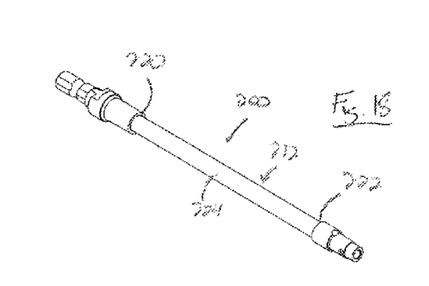
FIG. 18 is an isometric view of still another exemplary embodiment of an implement constructed according to the present disclosure.
Figure 19:
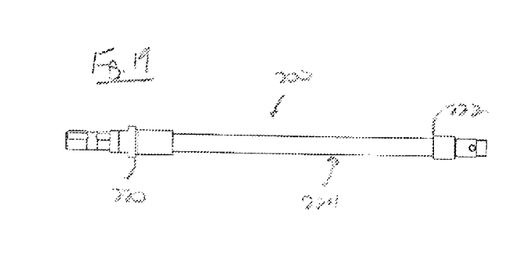
FIG. 19 is a side elevation view of the implement of FIG. 18.
Figure 20:
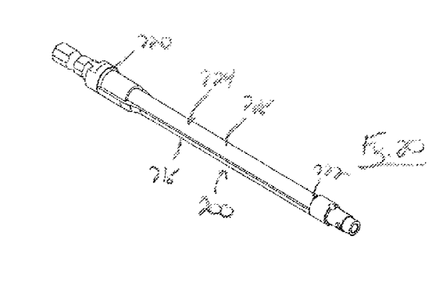
FIG. 20 is an isometric view of the implement of FIG. 18 after a first molding step.
Figure 21:
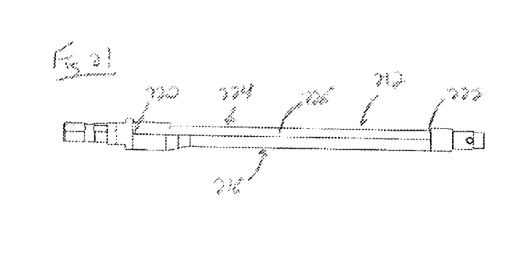
FIG. 21 is a side elevation view of the implement of FIG. 20.
Figure 22:
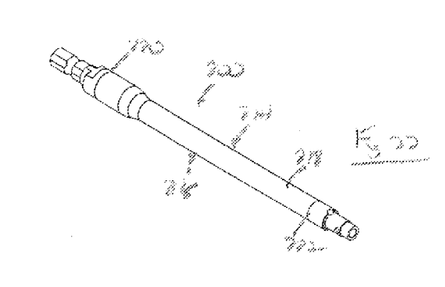
FIG. 22 is an isometric view of the implement of FIG. 18 after a second molding step.
Figure 23:
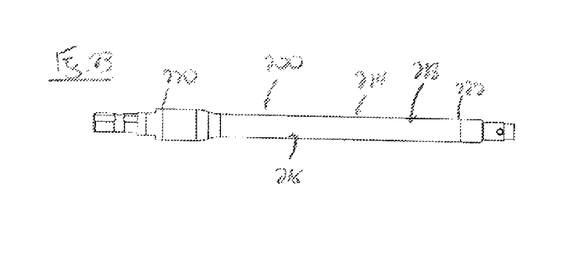
FIG. 23 is a side elevation view of the implement of FIG. 22.

In alternative embodiments, the portions 16' and 18' can be formed subsequently or simultaneously within a single mold in any suitable molding process. In the illustrated embodiment, the second portion 18' includes a number of spaced sections 104 disposed along the length of the core 12' alternating in a sequential manner between and joining the sections 102 to form the enclosure 14'. In this embodiment, as shown in FIGS. 15-17, the sections 102 and 104 form a seamless enclosure 14' around the core 12' complete with end caps 106 disposed over each end 20,22 of the core 12, which can be molded with either of the sections 102 or 104, or separately therefrom. The seamless enclosure 14' moves and/or flexes with the core 12' to retain the core 12' encased within the enclosure 14', such that the sterilization of the implement 100 does not contact the core 12'.

In a third embodiment of the implement 200 shown in FIGS. 18-23 illustrates the implement 200 as a flex driver. The implement 200 includes a flexible core 212, such as a spring or coil, with a pair of opposed ends 220 and 222 that, for example, is used to drive a fastener in a surgical procedure and may optionally include a mechanism suitable to assist in the driving of the fastener, such as a ratcheting or torque-limiting mechanism, among others. The ends 220 and 222 define a central section 224 therebetween, as best shown in FIGS. 18-21. In the embodiment shown in FIGS. 20 and 21, the first portion 216, which can be formed similarly to the first portion 16' in the prior embodiment, is molded onto the core 212 in a first mold in a first molding step over at least approximately one half of the central section 224 in a suitable process, such as those cited as examples for the molding of the first portion 16' in the prior embodiment. In this process, however, the ends 220 and 222 can function as stops for the flow of the material forming the first portion 216 at each end 220 and 222.

Subsequently, the core 212 can be removed from the first mold for positioning in a second mold, or simply rotated within the first mold to expose the uncovered portion 226 of the central section 224 within the second mold. One properly positioned, the second portion 218 can be formed over the uncovered section 226 to form the enclosure 214 over the central section 224 with the first portion 216 and without end caps, leaving the ends 220,222 exposed. In this configuration, the core 212 can be flexed as desired to properly orient the ends 220,222 to utilize the implement 200, but the enclosure 214 remains in close conformance with the core 212 to prevent debris from becoming positioned between the enclosure 214 and the core 212, and to limit the exposure of the core 212 to the sterilization environment when being sterilized for subsequent uses.

In alternative embodiments for either embodiment of the implement 100, 200, the process for molding the first portion 16',216 and/or second portion 18',218 can be performed in any number of separate molding steps in order to form the enclosure 14', 214 on the core 12',212 with the desired appearance, attributes or other characteristics with any desired number and/or types of different materials forming the portions 16',216 and/or 18',218.

Additional molding processes are also available for forming the enclosure 14, 14' or 214 around the core 12, 12' or 212. Examples of some of these types of molding processes are disclosed in U.S. patent application Ser. No. 14/168,600.

Various other embodiments of the present disclosure are contemplated as being within the scope of the filed claims particularly pointing out and distinctly claiming the subject matter regarded as the invention.

The invention claimed is:

1. A reusable surgical implement comprising:
   a) a core; and
   b) an enclosure formed around the core, the enclosure including a number of apertures extending through the enclosure without intersecting the core, wherein the enclosure is formed of an upper portion and a lower portion each with openings formed therein that are aligned with one another to form the apertures in the enclosure when the upper portion and lower portion are secured to one another around the core.

2. The reusable surgical implement of claim 1 wherein the core is formed of a shape memory material.

3. The reusable surgical implement of claim 1 wherein the implement is a reusable trial implant.

4. A reusable surgical implement comprising:
   a) a core; and
   b) an enclosure formed around the core, wherein the enclosure is formed of:
      i) a number of spaced first portions; and
      ii) a number of spaced second portions, wherein each second portion is positioned between spaced first portions.

5. The reusable surgical implement of claim 4 wherein the enclosure further includes end caps disposed on each end of the enclosure.

6. The reusable surgical implement of claim 4 wherein the implement is a rod template.

7. The reusable surgical implement of claim 4 wherein the implement is a flex driver.

* * * * *